United States Patent [19]

Clifford et al.

[11] 4,342,770

[45] Aug. 3, 1982

[54] OPTICALLY ACTIVE ISOMERS OF SUBSTITUTED PYRIDINE METHYL ESTERS OF CYCLOPROPANE CARBOXYLIC ACID AND THEIR USE AS INSECTICIDES

[75] Inventors: David P. Clifford; Robert A. Sewell, both of King's Lynn, England

[73] Assignee: Dow Chemical Company Limited, Norfolk, England

[21] Appl. No.: 161,532

[22] Filed: Jun. 20, 1980

[51] Int. Cl.$^3$ ............... C07D 213/70; C07D 213/64; A61K 31/44
[52] U.S. Cl. ................. 424/263; 546/270; 546/290; 546/300; 546/301; 546/302; 546/303
[58] Field of Search ............ 546/301, 302, 303, 300, 546/290, 270; 424/263

[56] References Cited

U.S. PATENT DOCUMENTS 4,163,787  8/1979  Malhotra et al. ............ 546/301

OTHER PUBLICATIONS

Burt, et al.; Pestic. Sci., (1974), 5, pp. 791–799.

Primary Examiner—Joseph Paul Brust
Attorney, Agent, or Firm—Ronald G. Brookens; S. Preston Jones

[57] ABSTRACT

Optionally active isomers of substituted pyridine methyl esters of cyclopropane carboxylic acids thereof are prepared and have been found to exhibit a higher degree of insecticidal activity than their unresolved parents and compositions containing said compounds are so employed as insecticides.

9 Claims, No Drawings

OPTICALLY ACTIVE ISOMERS OF SUBSTITUTED PYRIDINE METHYL ESTERS OF CYCLOPROPANE CARBOXYLIC ACID AND THEIR USE AS INSECTICIDES

DESCRIPTION OF PRIOR ART

U.S. Pat. No. 4,163,787 (British Patent Application No. 9658/78) is directed to substituted pyridine methyl esters of cyclopropane carboxylic acids and their use as insecticides. The specific esters taught are the parent esters of the optically active esters of the present invention. This patent discloses the cis and trans isomers of the compounds, however since there are three assymmetric carbon atoms in the ester compounds, the cis and trans forms each occur in the form of four optical isomers or eight optical isomers for the unresolved product containing both the cis and trans isomers.

SUMMARY OF THE INVENTION

The present invention is directed to optically active isomers of substituted pyridine methyl esters of cyclopropane carboxylic acids and compositions containing said active compounds and the use of such compositions in the kill and control of various insect pests. The compounds of the present invention correspond to the formula

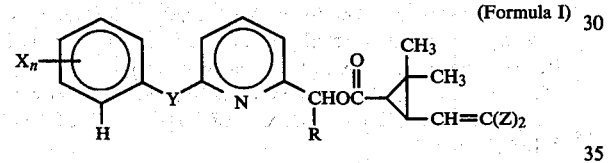

(Formula I)

wherein X independently represents alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo; n represents an integer of 0 to 2; Y represents oxygen or sulfur; R represents hydrogen, cyano or ethynyl and Z represents chloro or bromo.

In the present specification and claims, the term "alkyl of 1 to 4 carbon atoms" is employed to designate straight chain alkyls of 1 to 4 carbon atoms and branched chain alkyls of 3 or 4 carbon atoms such as, for example, methyl, ethyl, propyl, butyl, isopropyl, isobutyl, secondary butyl, tertiary butyl. In addition, cycloalkyl radicals of 3 or 4 carbon atoms can be employed. Such radicals are cyclopropyl and cyclobutyl.

In the present specification and claims, the terms "alkoxy of 1 to 4 carbon atoms", "alkylthio of 1 to 4 carbon atoms" and "alkylsulfonyl of 1 to 4 carbon atoms" are employed to designate alkoxy and alkylthio groups of the formula -Y-loweralkyl wherein Y is oxygen, sulfur or sulfonyl and alkyl is defined as hereinabove set forth for "alkyl of 1 to 4 carbon atoms".

It has been found that the optical isomers derived from the dextrorotatory (d) form of the cycopropane carboxylic acid have significantly greater insecticidal activity than those isomers derived from the levorotatory (l) form of the acid.

The present invention is specifically directed to the dextrorotatory (d) form of the two cis and two trans isomers available for each compound. These isomers can be separated individually and set forth as the (d)-cis-I, (d)-cis-II, (d)-trans-I and (d)-trans-II isomers for each compound.

The effect of cis-trans isomerism on the activity of the compounds is much less marked than (d), (l) isomerism and varies from insect to insect.

The active compounds of the present invention can be prepared by the general methods taught in U.S. Pat. No. 4,163,787. By following the procedures as taught by this patent, an appropriate substituted cyclopropane carboxylic acid or an acid chloride or ester derivative thereof, in the form of the (d)-cis or trans or mixed cis and trans isomers, is reacted with an appropriate substituted phenoxy or phenylthio pyridine reactant dependent upon the R group. For example, when R is hydrogen, the reactant can be a 6-(substituted phenoxy or phenylthio)-2-methyl pyridine or 6-(substituted phenoxy or phenylthio)-2-pyridine methanol. When R is ethynyl, the reactant can be an α-ethynyl-6-(substituted phenoxy or phenylthio)-2-pyridine methanol. When R is cyano, the reactant can be a cyano(6-(substituted phenoxy or phenylthio)-2-pyridine methanol (also known as a 6-(substituted phenoxy or phenylthio)-α-hydroxy-2-pyridine acetonitrile).

The reaction scheme can be characterized as follows:

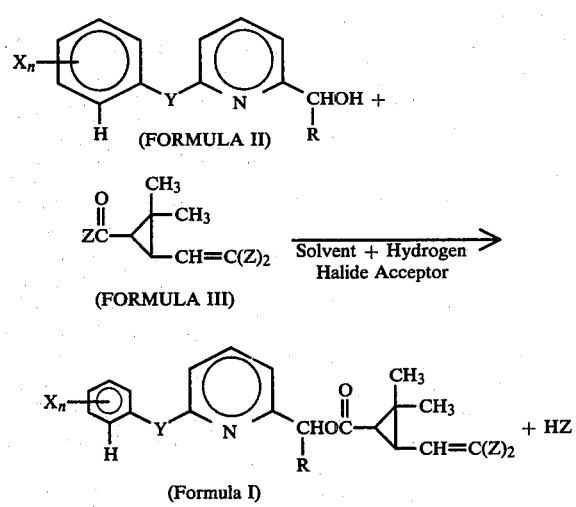

In carrying out this reaction, the appropriate phenoxy or phenylthio pyridine methanol or substituted methanol and the appropriate 2,2-dimethyl-3-(2,2-dihalovinyl)cyclopropane carboxylic acid halide are mixed together in substantially equimolar amounts, with the solvent, conveniently at room temperature. The hydrogen halide acceptor is thereafter added to the above mixture, with stirring. The mixture is stirred for from 0.1 to 24 hours and the mixture is then diluted with water and extracted thoroughly with a conventional solvent such as, for example, diethyl ether, hexane, methylene chloride or chloroform. The solvent extract is water washed, dried and concentrated under reduced pressure and if desired, purified by distillation or other conventional methods.

Representative solvents for use in carrying out this reaction include diethyl ether, methylene chloride, glyme and hexane.

Representative hydrogen halide acceptors include conventional bases such as, for example, triethylamine, pyridine, dimethylaniline and the conventional alkali metal bases such as sodium hydroxide, potassium hydroxide, sodium carbonate, potassium bicarbonate, sodium bicarbonate and the like.

In accordance with the present invention, it should be understood that the various geometric isomers as well as the mixed compound can be prepared by the procedures taught herein.

DESCRIPTION OF SOME PREFERRED EMBODIMENTS

The following examples illustrate the present invention and the manner by which it can be practiced but, as such, should not be construed as limitations upon the overall scope of the same.

EXAMPLE I:
3-(2,2-Dibromoethenyl)-2,2-dimethylcyclopropane carboxylic acid:cyano(6-phenoxy-2-pyridinyl)methyl ester (d)-cis isomers 1 and 2

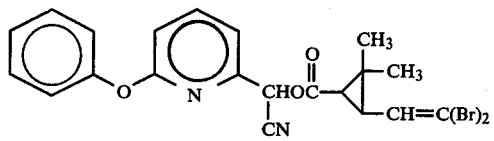

A solution was prepared by admixing 10.0 grams (g) (0.0336 moles (m)) the (d)-cis isomer of 2,2-dimethyl-3-(2,2-dibromoethenyl)cyclopropane carboxylic acid with 20 milliliters (ml) of thionyl chloride, 0.25 ml of dimethylformamide and 100 ml of methylene chloride. This solution was stirred at room temperature for 30 minutes. The solvent was then removed by evaporation under reduced pressure.

The (d)-cis-isomer of 2,2-dimethyl-3-(2,2-dibromoethenyl)cyclopropane carboxylic acid chloride thus prepared was mixed with 6.6 g (0.0336 m) of 6-phenoxypicolinaldehyde and 100 ml of toluene. The resulting mixture was mixed with a solution of 3.3 g (0.067/3.76 m) of sodium cyanide in 20 ml of water at 15° C. and the reaction mixture stirred overnight.

The aqueous and organic layers which formed were separated and the organic layer was washed with dilute aqueous sodium hydroxide and filtered through silica gel.

The solvent was removed by evaporation under reduced pressure leaving 16 g of the crude product (92 percent purity by gas-liquid chromatography (glc)). The product was purified by liquid chromatography with two fractions being recovered.

The first fraction was crystallized twice from hexane and the product was recovered as a white solid in a yield of 5.7 g having a specific rotation of $[\alpha]_D^{23} = -7.72$ (0.5830 g/10, CHCl$_3$) and which melted at 65°-66° C. Upon analysis, this fraction called the (d)-cis-1 isomer, was found to have carbon, hydrogen and nitrogen contents of 50.11, 3.56 and 5.54 percent, respectively, as compared with the theoretical contents of 49–82, 3.58 and 5.53 percent, respectively, calculated for the above named compound.

The second fraction was redramatographed and the pale yellow oil which was recovered contained about 1% of the first ester product (first fraction product). The product had a specific rotation of $[\alpha]_D^{23} = +10.89$ (0.5234 g/10, CHCl$_3$) and a refractive index of n(23/d) = 1.5783. Upon analysis, this fraction, called the (d)-cis-2 isomer, was found to have carbon, hydrogen and nitrogen contents of 48.75, 3.52 and 5.32 percent, respectively, as compared with the theoretical contents of 49.82, 3.58 and 5.93 percent, respectively, calculated for the above named compound.

EXAMPLE II:
3-(2,2-Dichloroethenyl)-2,2-dimethylcyclopropane carboxylic acid:cyano(6-phenoxy-2-pyridinyl)methyl ester-d-cis isomers 1 and 2

A solution was prepared containing 8.0 g (0.038 m) of the (d)-cis isomer of 3-(2,2-dichloroethenyl)-2,2-dimethylcyclopropane carboxylic acid, 6.0 g (0.058 m) of thionyl chloride and 100 ml of dichloromethane. The mixture was refluxed for 1½ hours. The solvent and unreacted thionyl chloride were removed by evaporation under reduced pressure. The resulting solution and 3.52 g (0.0176 m) of 6-phenoxy-2-picolinaldehyde in 35 ml of carbon tetrachloride were added dropwise over an hour to a stirred solution containing 1.76 g (0.035 m) of sodium cyanide, 100 milligrams (mg) (0.35 millimole) in 10 ml of water. The mixture was stirred for 2 hours at ~22° C. The reaction mixture was washed with a saturated sodium bicarbonate solution followed by a water wash. After drying, the solvent was removed under reduced pressure to give a brown oil. Separation of the product isomers from the 3-(2,2-dichloroethenyl)-2,2-dimethylcyclopropane carboxylic acid:cyano(6-phenoxy-2-pyridinyl)methyl ester product by preparative liquid chromatography to give 0.6 g of the (d)-cis-1 isomer which had a specific rotation of $[\alpha]_D^{23} = -23.2°$ (C 1.360, acetone) and 0.55 g of the (d)-cis-2 isomer which had a specific rotation of $[\alpha]_D^{23} = +22.0°$ (C 1.183, acetone).

By following the preparative procedures as outlined in the above examples and employing the appropriate substituted cyclopropane carboxylic acid, acid chloride or ester derivative thereof in the form of the (d)-cis or trans mixed cis and trans isomers and the appropriate phenoxy or phenylthio pyridine, the (d)-cis-, trans- and mixtures thereof of the following compounds of Table I are prepared.

TABLE I

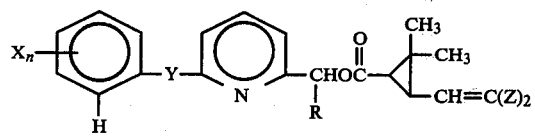

| Compound No. | $X_n$ | Y | R | Z | Molecular Weight |
|---|---|---|---|---|---|
| 3 | 3-CH$_3$ | O | —CN | Cl | 431.31 |
| 4 | 2-CH$_3$ | O | —CN | Cl | 431.31 |
| 5 | 4-Cl | O | —CN | Cl | 451.74 |
| 6 | 3-CF$_3$ | S | —CN | Cl | |
| 7 | 3-CF$_3$ | S | —H | Br | |
| 8 | H | O | —H | Cl | |
| 9 | 3-F | O | —CN | Cl | |
| 10 | H | O | —C≡CH | Cl | |
| 11 | 3-CF$_3$ | O | —CN | Cl | 485.29 |
| 12 | 2-CF$_3$ | O | —C≡CH | Cl | 484.31 |
| 13 | 4-F | O | —CN | Cl | 435.28 |
| 14 | 4-CH$_3$ | O | —CN | Cl | 431.31 |
| 15 | 4-C$_2$H$_5$ | O | —CN | Cl | 445.34 |
| 16 | 3-C$_2$H$_5$ | O | —CN | Cl | 445.34 |
| 17 | 2-C$_2$H$_5$ | S | —C≡CH | Cl | |
| 18 | 3-i-C$_3$H$_7$ | S | —H | Br | 530.36 |
| 19 | 3-i-C$_3$H$_7$ | O | —CN | Cl | 459.38 |
| 20 | 4-Br | O | —CN | Cl | 460.74 |

TABLE I-continued

Structure: $X_n$-(phenyl)-Y-(pyridine with N)-CHOC(=O)-C(CH_3)_2-CH=C(Z)_2, with R on the CHOC carbon.

| Compound No. | $X_n$ | Y | R | Z | Molecular Weight |
|---|---|---|---|---|---|
| 21 | 2,4-Br$_2$ | S | —H | Br | 655.06 |
| 22 | — | S | —CN | Cl | 433.36 |
| 23 | 4-OCH$_3$ | S | —H | Br | 528.30 |
| 24 | 2-OCH$_3$ | O | —CN | Br | |
| 25 | 3,4-methylenedioxy | O | —CN | Cl | 459.33 |
| 26 | 2-OC$_4$H$_9$ | O | —CN | Cl | 489.40 |
| 27 | 4-OC$_4$H$_9$ | S | —CN | Br | 594.38 |
| 28 | 4-OC$_4$H$_9$ | O | —CN | Cl | 489.40 |
| 29 | 3,5-(CH$_3$)$_2$ | O | —H | Cl | |
| 30 | 3,5-(CH$_3$)$_2$ | O | —CN | Cl | 445.34 |
| 31 | — | O | —C≡CH | Cl | 416.31 |
| 32 | 2-F | O | —CN | Cl | 435.28 |
| 33 | 4-SCH$_3$ | O | —CN | Cl | 463.39 |
| 34 | 3,4-(CH$_3$)$_2$ | O | —CN | Cl | 445.35 |
| 35 | 4-OCH$_3$ | O | —CN | Cl | 447.32 |
| 36 | 3,5-(SCH$_3$)$_2$ | S | —C≡CH | Cl | |
| 37 | 3-CH$_3$; 5-C$_4$H$_9$ | O | —CN | Cl | 455.43 |
| 38 | 3,5-(OC$_4$H$_9$)$_2$ | O | —H | Cl | 524.49 |
| 39 | — | O | —CN | Br | |
| 40 | 3-t-C$_4$H$_9$ | O | —CN | Cl | 473.40 |
| 41 | 3-BR | O | —CN | Cl | 496.20 |
| 42 | 2-OCH$_3$ | O | —CN | Cl | 447.32 |
| 43 | 4-SC$_4$H$_9$ | O | —CN | Br | 594.38 |
| 44 | 3-Cl | O | —CN | Cl | 451.74 |
| 45 | 3,5-(CF$_3$)$_2$ | S | —CN | Cl | |
| 46 | 3,5-(CF$_3$)$_2$ | S | —H | Cl | |
| 47 | 3,5-(OC$_4$H$_9$)$_2$ | O | —CN | Cl | 561.51 |
| 48 | 2-CF$_3$ | O | —C≡CH | Br | 641.22 |
| 49 | 3,4-Cl$_2$ | O | —CN | Cl | 486.19 |
| 50 | 3-OCH$_3$ | O | —CN | Cl | 447.32 |
| 51 | 4-SC$_4$H$_9$ | O | —CN | Cl | 505.45 |
| 52 | 4-SO$_2$CH$_3$ | O | —CN | Cl | 495.39 |
| 53 | 4-SO$_2$C$_4$H$_9$ | O | —CN | Cl | 537.47 |
| 54 | 2-Cl; 4-Br | S | —H | Br | 575.15 |
| 55 | 2-Cl; 4-CF$_3$ | O | —CN | Cl | 505.73 |
| 56 | 3-OCH$_3$; 4-OC$_2$H$_5$ | S | —CN | Cl | 477.37 |
| 57 | 2-CH$_3$; 4-Cl | O | —CN | Cl | 453.76 |
| 58 | 3-CH$_3$; 4-Cl | O | —CN | Cl | 453.76 |
| 59 | 3,4-Cl$_2$ | O | —CN | Cl | 486.19 |
| 60 | 3,5-Cl$_2$ | O | —CN | Cl | 486.19 |
| 61 | — | O | —C≡CH | Br | 505.22 |
| 62 | — | S | —C≡CH | Cl | 432.37 |
| 63 | 4-Cl | O | —C≡CH | Cl | 450.75 |
| 64 | 4-F | O | —C≡CH | Cl | 434.30 |
| 65 | 4-F | S | —C≡CH | Cl | |
| 66 | 3-Cl | O | —C≡CH | Cl | 450.75 |
| 67 | 4-OCH$_3$ | O | —C≡CH | Cl | 446.33 |
| 68 | 4-CH$_3$ | O | —C≡CH | Cl | 430.33 |
| 69 | 4-CH$_3$ | S | —C≡CH | Br | 535.31 |
| 70 | — | O | H | Cl | 392.29 |
| 71 | — | O | H | Br | |
| 72 | 4-Cl | O | H | Cl | 426.73 |
| 73 | 4-F | O | H | Cl | 410.28 |
| 74 | 3-Cl | O | H | Cl | 426.73 |
| 75 | 4-OCH$_3$ | O | H | Cl | 399.26 |
| 76 | 4-CH$_3$ | O | H | Cl | 392.29 |
| 77 | 4-CH$_3$ | S | H | Br | 497.26 |
| 78 | 4-Cl | S | H | Br | |
| 79 | 3-Cl | S | H | Br | 531.71 |
| 80 | 4-F | S | H | Br | 515.25 |
| 81 | 4-OCH$_3$ | S | H | Cl | |

PREPARATION OF STARTING MATERIALS

The phenoxy or phenylthio pyridine methanol or substituted methanols employed as starting materials are known materials and can be prepared as taught in U.S. Pat. No. 4,163,787.

The (d)-cis- and trans-2,2-dimethyl-3-(2,2-dihaloethenyl)cyclopropane carboxylic acid employed as starting materials are known materials which can be prepared as set forth in Burk et al. "Pesticide Science" (1974), volume 5, pages 791–799.

These acids can be converted to the corresponding acid halide by conventional procedures such as, for example, reacting the appropriate 2,2-dimethyl-3-(2,2-dihaloethenyl)cyclopropane carboxylic acid with a thinoyl halide such as thionyl chloride, thionyl bromide or thionyl fluoride or a phosphorous halide such as phosphorus trichloride or phosphorus oxychloride at a temperature of from about room temperature to the reflux temperature of the mixture in the presence of an organic solvent such as benzene, hexane or a benzene-hexane mixture. Upon the completion of the reaction, the solvent is removed, leaving the desired product.

These acids can also be converted to the corresponding alkyl esters by conventional procedures such as, for examples, reacting the appropriate 2,2-dimethyl-3-(2,2-dihaloethenyl)cyclopropane carboxylic acid with an alkanol, preferably a lower alkanol of from 1 to 4 carbon atoms in the presence of a mineral acid.

The (d)-cis- and trans-2,2-dimethyl-3-(2,2-dibromoethenyl)cyclopropane carboxylic acid can also be prepared by bromine exchange with the appropriate chloro compound (prepared as set forth herein above). In such procedure, one mole of the acid or ester thereof is reacted with ~2 moles of aluminum bromide in the presence of a solvent such as dibromomethane at a temperature of from about 0° to about 10° C.

Because of the "quick knockdown", the subject compounds are particularly suitable for the control, inside houses, barns, warehouses, public buildings, and the like, of pests, including cockroaches, such as the German cockroach, American cockroach, and brown-banded cockroach; beetles, such as the black-carpet beetle, confused flour beetle, saw-tooth grain beetle, and larder beetle; spiders, silverfish, bedbugs; fleas such as those on bedding used by household pets, and flea larvae; mosquitos; boxelder bugs; spiders; mites; ants; centipedes; and flies, such as hornfly, stable fly and facefly and the common housefly. The subject compounds are highly effective for such indoor control of insect pests and thus are particularly adapted for such employment. In addition, the subject compounds are also useful for the control of lice and ticks and other insects parasitic to animals.

The new compounds of the present invention are very effective for the control of the many insect pests found on the roots or aerial portions of growing plants, including aphids, scale, mites, and chewing and sucking insects, such as leafhopper, Southern army worm, two-spotted spider mite, cotton aphid, cabbage looper, western spotted cucumber beetle, bollworm, codling moth, beet armyworm, and tobacco budworm.

The subject compounds, when applied to plants, plant parts, and their habitats to protect the plants from the attack of insect pests, exhibit residual control of the insects over only a relatively short period of time thereby not having appreciable build-up in the environment.

In some procedures, the compounds can be vaporized or sprayed or distributed as aerosols into the air, or onto surfaces in contact with the air. In such applications, the compounds manifest the useful properties hereinbefore described.

The methods of the present invention comprise contacting an insect with an insecticidally effective or inactivating amount of one of the compounds of the present invention.

The contacting can be effected by application of the compound to the habitat of the insects. Representative habitats include soil, air, water, food, vegetation, inert objects, stored matter such as grains, other animal organisms, and the like. The inactivation can be lethal, immediately, or with delay, or can be a sub-lethal, one in which the inactivated insect is not able to carry out one or more of its normal life processes. This latter situation prevails when one of the systems of the insect, typically the nervous system, is seriously disturbed. A preferred embodiment of the present invention comprises the employment of the present method for the kill and control of insects; such employment gives excellent results, particularly in control of insects that have developed resistance against other pest-control substances.

The inactivation of an insect by the application of an insecticidally effective or inactivating amount of one of the presently claimed compounds is critical to the method of the present invention. The compound can sometimes be employed in unmodified form. Frequently, however, for easier application, the compound is modified by the employment with it of a pesticidal adjuvant or inert carrier therefor. Thus, for example, the present compounds are of very low solubility in water but are relatively soluble in oils, including plant essential oils. Therefore, the practical enjoyment of the beneficial utilities of the present compounds often requires that the compound be composited with one or more pesticidal adjuvant substances, and the resulting compositions are comprehended within the present invention.

The compositions can be formulated in various forms, such as emulsifiable concentrates, wettable powders, flowable suspension dusts, granules, microencapsulated granules, fine granules, oil sprays, aerosols, heating fumigants (e.g. mosquito coils, electric mosquito killer mat, etc.), fogging mists, non-heating fumigants and poisonous baits and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising one or more of the presently claimed compounds, an organic liquid as a solvent and carrier therefor, and a propellant material. Numerous other embodiments will become available to those skilled in the art in view of the teachings set forth hereinbelow.

The exact concentration of the active compounds in a composition thereof with an adjuvant therefor can vary; it is only necessary that the active compounds be present in a sufficient amount so as to make possible the application of an insecticidally effective or inactivating dosage. Generally, for practical applications, the active compounds can be broadly applied to insect pest organisms or their habitat in compositions containing from about 0.00001 percent to about 98 percent by weight of the active compound.

In the preparation of dust compositions, the product can be compounded with any of the finely divided carrier solids such as pyrophyllite, diatomaceous earth, gypsum and the like. In such operations, the finely divided carrier is ground or mixed with one or more of the active compounds, as active agent, or wetted with a solution of the active agent in a volatile organic solvent. Similarly, dust compositions containing the active product can be similarly compounded from various of the solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, one of the compounds or a dust concentrate composition containing such compound can be incorporated in intimate mixture with surface active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the compounds of the present invention can be compounded with a suitable water-immiscible organic liquid and surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the non-ionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, the compound or a composition containing the compound is applied to the insects to be controlled directly, or by means of application to a portion or portions of their habitat in any convenient manner, for example, by means of hand dusters or sprayers or by simple mixing with the food to be ingested by the organisms. Application to the foilage of plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane. The present invention also comprehends the employment of compositions comprising one of the compounds, an adjuvant, and one or more other biologically active materials, such as insecticides, fungicides, miticides, bactericides, nematocides, and the like.

A preferred and especially convenient matter for the application of one or more of the present products comprises the use of a self-pressurized pack formulation which can be used, for example, as a space or surface spray. Such a formulation can comprise one or more of the compounds, an organic liquid as a solvent and vehicle therefor, and a propellant material which can be a condensed and compressed gas or a substance which, at room temperature, is a gas under atmospheric pressure but which liquifies under superatmospheric pressure. Where the propellant material is of the latter type, the self-pressurized pack formulation is often spoken of as an aerosol. Representative propellants include propane, butane, nitrogen, and the fluorinated hydrocarbons, such as dichlorodifluoromethane and trichlorofluoromethane. Generally, the propellant constitutes from 25 to 95 percent by weight of the total self-pressurized pack. As vehicle, there can be employed any liquid in which the desired amount of product is capable of being dispersed; preferred vehicles include petroleum distillates, kerosene, and methylene chloride. The self-pressurized pack formulation can also include other materials, such as other biologically active agents or synergists. For further discussion of the use of self-pressurized pack formulations, see U.S. Pat. Nos. 1,892,750 and 2,321,023.

The compositions of the present invention will be illustrated in further detail below with reference to the examples, but the kinds and mixing proportions of compounds and additives are not limited to those shown in the examples but are variable within wide ranges. In the Examples set forth hereinafter, the compounds employed are referred to by the compound number as hereinabove set forth. All parts are based on weight percent of the total composition.

EXAMPLE III

A dust composition is prepared by admixing and pulverizing 3 parts of one of the compounds numbered 2, 3, 4, 8, 9, 11, 16, 17, 22, 23, 26, 36, 53 or 54 with 97 parts of Barden clay to obtain a composition containing 3 percent of the active ingredient. In application, the composition is dusted as such.

EXAMPLE IV

50 Parts of one of the compounds numbered 35, 54 or 55; 5 parts of a wetting agent (alkylbenzenesulfonate type) and 45 parts of diatomaceous earth are thoroughly pulverized and mixed together to obtain a wettable powder containing 50 percent of active ingredient. In application, the powder is diluted with water and used as a spray.

EXAMPLE V

A mixture of 5 parts of one of the compounds numbered 2, 5, 7, 13, 43, 44, 51, 54 or 55; 93.5 parts of clay and 1.5 parts of polyvinyl alcohol are thoroughly kneaded with water and the mixture granulated and dried. The granule composition contains 5 percent of the active ingredient and can be applied as such.

EXAMPLE VI

25 Parts of compound numbered 49, 50 parts of toluene and 25 parts of Atlox 3404F ® (proprietary material of Imperial Chemical Industries, U.S. which is a polyoxyethylene alkyl aryl ether-alkyl aryl sulfonate blend) are mixed together to obtain an emulsifiable concentrate having an active ingredient concentration of 25 percent. In application, the concentrate is diluted with water and sprayed.

EXAMPLE VII 7.6 Parts of one of the compounds numbered 17, 20, 46, 48, 50, 51 or 54; 80.4 parts of purified xylene and 12.0 parts of Atplus 300F ® (proprietary material of Imperial Chemical Industries, U.S. which is a polyoxyethylene sorbitol ester) are mixed together to obtain an emulsifiable concentrate having an active ingredient concentration of 7.6%. In application, the preparation is diluted with water and used as a spray.

EXAMPLE VIII

1 Part of one of the compounds numbered 8, 11, 16, 37, 42 or 44 is mixed with 99 parts of purified Kerosene to obtain an oil preparation having an active ingredient concentration of 1 percent. In application, the composition can be atomized or sprayed as is.

The control of pest organisms by the contacting thereof with one or more of the compounds of the present invention is illustrated by the following examples.

EXAMPLE VIX

Aqueous acetone solutions containing various concentrations of one of 3-(2,2-dichloroethenyl)-2,2-dimethylcyclopropane carboxylic acid:cyano(6-phenoxy-2-pyridinyl)methyl ester in the form of its (d)-cis-1, (d)-cis-2, (d)-trans-1 and (d)-trans-2 isomers were prepared by diluting acetone concentrates of the compound with predetermined amounts of water and acetone. Cotton leafworm larvae, third instar, (*Spodoptera littoralis*) (10 per treatment) were placed on cotton leave and then both were sprayed with one of the solutions applied at a rate equal to about 600 liters per hectare. The larvae were allowed to feed on the leaves for 48 hours after which the amount of test compound necessary to give a 90 percent kill and control ($LC_{90}$) of the larvae was determined. During the 48 hour period, the treated plants were maintained under conditions conducive to good plant and insect growth. The results of this test is as follows:

TABLE II

| Compound | Amount of Test Compound In P.P.M. to give $LC_{90}$ |
|---|---|
| 3-(2,2-dichloroethenyl)-2,2-dimethyl cyclopropane carboxylic acid:cyano(6-phenoxy-2-pyridinyl methyl ester as | |
| (d)-cis-1 isomer | 1.5 |
| (d)-cis-2 isomer | 1.5 |
| (d)-trans-1 isomer | 1 |
| (d)-trans-2 isomer | 1.0 |

In other operations, employing the above procedure, the following results were obtained for *Heliothio armigera*.

TABLE III

| Compound | Amount of Test Compound In P.P.M. to give $LC_{90}$ |
|---|---|
| 3-(2,2-dichloroethenyl)-2,2-dimethyl cyclopropane carboxylic acid:cyano(6-phenoxy-2-pyridinyl methyl ester as | |
| (d)-cis-1 isomer | 1.0-2.5 |
| (d)-cis-2 isomer | 2.5 |
| (d)-trans-1 isomer | 5.0-7.5 |

TABLE III-continued

| Compound | Amount of Test Compound In P.P.M. to give LC$_{90}$ |
| --- | --- |
| (d)-trans-2 isomer | 1.0–2.5 |

In other operations, employing the above procedure, the following results were obtained for *Pectinophora gossypiella*.

TABLE IV

| Compound | Amount of Test Compound In P.P.M. to give LC$_{90}$ |
| --- | --- |
| 3-(2,2-dichloroethenyl)-2,2-dimethyl cyclopropane carboxylic acid:cyano(6-phenoxy-2-pyridinyl methyl ester as | |
| (d)-cis-1 isomer | 10.0–15.5 |
| (d)-cis-2 isomer | 20.0 |
| (d)-trans-1 isomer | 15.0–20.0 |
| (d)-trans-2 isomer | 15.0 |

What is claimed is:

1. An optically active dextrorotatory (d) form of an isomer of the compound 3-(2,2-dichloroethenyl)-2,2-dimethylcyclopropane carboxylic acid:cyano(6-phenoxy-2-pyridinyl)methyl ester.

2. The isomer as defined in claim 1 which is (d)-cis-3-(2,2-dichloroethenyl)-2,2-dimethylcyclopropane carboxylic acid:cyano(6-phenoxy-2-pyridinyl)methyl ester.

3. The isomer as defined in claim 1 which is (d)-trans-3-(2,2-dichloroethenyl)-2,2-dimethylcyclopropane carboxylic acid:cyano(6-phenoxy-2-pyridinyl)methyl ester.

4. An insecticidal composition comprising an inert carrier in intimate admixture with an insecticidally effective amount of an optically active dextrorotatory (d) form of an isomer of the compound 3-(2,2-dichloroethenyl)-2,2-dimethylcyclopropane carboxylic acid:cyano(6-phenoxy-2-pyridinyl)methyl ester.

5. The composition as defined in claim 4 wherein the compound is (d)-cis-3-(2,2-dichloroethenyl)-2,2-dimethylcyclopropane carboxylic acid:cyano(6-phenoxy-2-pyridinyl)methyl ester.

6. The composition as defined in claim 4 wherein the compound is (d)-trans-3-(2,2-dichloroethenyl)-2,2-dimethylcyclopropane carboxylic acid:cyano(6-phenoxy-2-pyridinyl)methyl ester.

7. A method for the kill and control of insects which comprises contacting said insects or their habitat with a composition comprising an inert carrier in intimate admixture with an insecticidally effective amount of an optically active dextrorotatory (d) form of an isomer of the compound 3-(2,2-dichloroethenyl)-2,2-dimethylcyclopropane carboxylic acid:cyano(6-phenoxy-2-pyridinyl)methyl ester.

8. The method as defined in claim 7 wherein the active ingredient is (d)-cis-3-(2,2-dichloroethenyl)-2,2-dimethylcyclopropane carboxylic acid:cyano(6-phenoxy-2-pyridinyl)methyl ester.

9. The method as defined in claim 7 wherein the active ingredient is (d)-trans-3-(2,2-dichloroethenyl)-2,2-dimethylcyclopropane carboxylic acid:cyano(6-phenoxy-2-pyridinyl)methyl ester.

* * * * *